United States Patent
Bugge et al.

(10) Patent No.: US 9,041,793 B2
(45) Date of Patent: May 26, 2015

(54) SCANNING MICROSCOPE HAVING AN ADAPTIVE SCAN

(75) Inventors: Cliff Bugge, Portland, OR (US); Brandon van Leer, Cornelius, OR (US)

(73) Assignee: FEI COMPANY, Hillsboro, OR (US)

( * ) Notice: Subject to any disclaimer, the term of this patent is extended or adjusted under 35 U.S.C. 154(b) by 442 days.

(21) Appl. No.: 13/474,176

(22) Filed: May 17, 2012

(65) Prior Publication Data
US 2013/0307957 A1    Nov. 21, 2013

(51) Int. Cl.
| | |
|---|---|
| H04N 7/18 | (2006.01) |
| H01J 37/22 | (2006.01) |
| H01J 37/26 | (2006.01) |
| H01J 37/28 | (2006.01) |
| G02B 21/00 | (2006.01) |

(52) U.S. Cl.
CPC ............ H01J 37/222 (2013.01); H01J 37/265 (2013.01); H01J 37/28 (2013.01); H01J 2237/2813 (2013.01); G02B 21/002 (2013.01)

(58) Field of Classification Search
CPC ... G02B 21/002; G02B 21/367; H01J 37/222; H01J 37/28; H01J 37/265; H01J 2237/2813; C12N 15/8247; C07K 14/415; G01Q 60/00
USPC .......................................................... 348/79
See application file for complete search history.

(56) References Cited

U.S. PATENT DOCUMENTS

| | | | |
|---|---|---|---|
| 6,889,113 B2 | 5/2005 | Tasker et al. | |
| 7,308,334 B2 | 12/2007 | Tasker et al. | |
| 7,348,556 B2 | 3/2008 | Chitturi et al. | |
| 7,664,566 B2 | 2/2010 | Tasker et al. | |
| 8,350,237 B2 | 1/2013 | Tanner | |
| 2004/0158409 A1* | 8/2004 | Teshima et al. | 702/22 |
| 2005/0044519 A1* | 2/2005 | Sengupta et al. | 716/11 |
| 2005/0053858 A1* | 3/2005 | Yuasa et al. | 430/109.4 |
| 2005/0121611 A1* | 6/2005 | Kimba et al. | 250/311 |
| 2006/0038125 A1* | 2/2006 | Tsuneta et al. | 250/310 |
| 2007/0194235 A1* | 8/2007 | Kimba et al. | 250/310 |
| 2008/0073527 A1* | 3/2008 | Nakazawa et al. | 250/307 |
| 2008/0073587 A1* | 3/2008 | Schmidt et al. | 250/492.21 |
| 2009/0129660 A1* | 5/2009 | Gregson | 382/133 |

(Continued)

FOREIGN PATENT DOCUMENTS

| | | |
|---|---|---|
| EP | 2416165 | 2/2012 |
| EP | 2584362 | 4/2013 |

OTHER PUBLICATIONS

Celebi, M. Emre, et al., "Contrast enhancement in dermoscopy images by maximizing a histogram bimodality measure," Proceedings of the IEEE International Conference on Image Processing, 2009, 4 pgs.

(Continued)

Primary Examiner — Shan Elahi
(74) Attorney, Agent, or Firm — Scheinberg & Associates, PC; Michael O. Scheinberg; John E. Hillert (57) ABSTRACT

A method of using a scanning microscope to rapidly form a digital image of an area. The method includes performing an initial set of scans to form a guide pixel set for the area and using the guide pixel set to identify regions representing structures of interest in the area. Then, performing additional scans of the regions representing structures of interest, to gather further data to further evaluate pixels in the regions, and not scanning elsewhere in the area.

11 Claims, 7 Drawing Sheets

(56) References Cited

U.S. PATENT DOCUMENTS

| | | | |
|---|---|---|---|
| 2009/0153659 A1* | 6/2009 | Landwehr et al. | 348/135 |
| 2009/0274359 A1* | 11/2009 | Nakazawa et al. | 382/132 |
| 2010/0040266 A1* | 2/2010 | Perz et al. | 382/128 |
| 2012/0001070 A1* | 1/2012 | Takagi | 250/310 |
| 2012/0138795 A1* | 6/2012 | Nakazawa et al. | 250/310 |
| 2012/0262563 A1* | 10/2012 | Marcelpoil et al. | 348/79 |

OTHER PUBLICATIONS

Unknown, "Dexis Imaging Software—Overview," http://www.dexis.com/index.php?option=content&task=view&id=219, retrieved Apr. 9, 2013, 2 pgs.

Unknown, "Dexis: Quick Reference Guide," 4 pgs.

Unknown, "Image Diagnost," http://www.imagediagnost.de/english/cadmethoden.en.html#3, retrieved Apr. 9, 2013, 6 pgs.

* cited by examiner

SCANNING MICROSCOPE HAVING AN ADAPTIVE SCAN

TECHNICAL FIELD OF THE INVENTION

The present invention relates to a method and an apparatus incorporating the method for adaptive scanning in a scanning microscope.

BACKGROUND OF THE INVENTION

Forming a high resolution digital image of a volume by a scanning electron microscope (SEM)/focused ion beam (FIB) dual beam device is an increasingly useful tool in the fields of biology (examination of tissue) and natural resource exploitation (examination of core samples). In this technique the FIB iteratively slices the volume to be imaged, thereby progressively exposing surfaces and the SEM makes an image of each exposed surface. This process may entail the collection of an immense amount of data, typically in the giga pixel range. This data collection can be very time-consuming, taking anywhere from 4 to 60 hours. Having to wait such a long period of time can represent a major roadblock to researchers attempting to learn more about the nature of a problem as quickly as possible. Moreover, it limits the throughput of a device.

SUMMARY OF THE INVENTION

Embodiments of a method and apparatus are provided herein for scanning a specimen to form digital imagery, with a set of guide data initially gathered and used to eliminate from further scanning regions of the specimen that are determined to be not of interest. The elimination from scanning of the regions that are not of interest speeds up scanning, making the process more efficient.

In a first separate aspect, the present invention may take the form of a method of using a scanning microscope to rapidly form a digital image of an area. The method includes performing an initial set of scans to form a guide pixel set for the area and using the guide pixel set to identify regions representing structures of interest in the area. Then, performing additional scans of the regions representing structures of interest, to gather further data to further evaluate pixels in the regions, and not scanning elsewhere in the area.

In a second separate aspect, the present invention may take the form of a scanning microscope assembly, adapted to perform a scan of an area, and as a part of performing the scan of the area, adapted to perform an initial set of scans to form a guide pixel set for the area and then to use the guide pixel set to identify regions representing structures of interest in the area. Then, the scanning microscope assembly performs additional scans of the regions representing structures of interest by scanning the area using a scanning beam, to gather further data to further evaluate pixels in the regions, and does not scan elsewhere in the area.

In a third separate aspect, the present invention may take the form of a method of forming an image of an area containing regions of interest and regions not of interest using a scanning imaging device. The method includes performing a brief scan, thereby collecting less accurate information than possible, but also taking less time and using data from the brief scan to determine pixels representing regions not of interest. Then, performing a scan at a slower rate, but not scanning pixels determined to represent regions not of interest, thereby completing the scan more quickly.

In a fourth separate aspect, the present invention may take the form of a scanning electron microscope assembly including a data entry sub assembly, adapted to permit a user to input dimensional characteristics of structures of interest in a specimen to be scanned, and wherein the dimensional characteristics affect scanning of the specimen. Examples of such dimensional characteristics include, but are not limited to, the type of materials of the specimen to be scanned and orientations of internal features of the specimen.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

Figure 1:
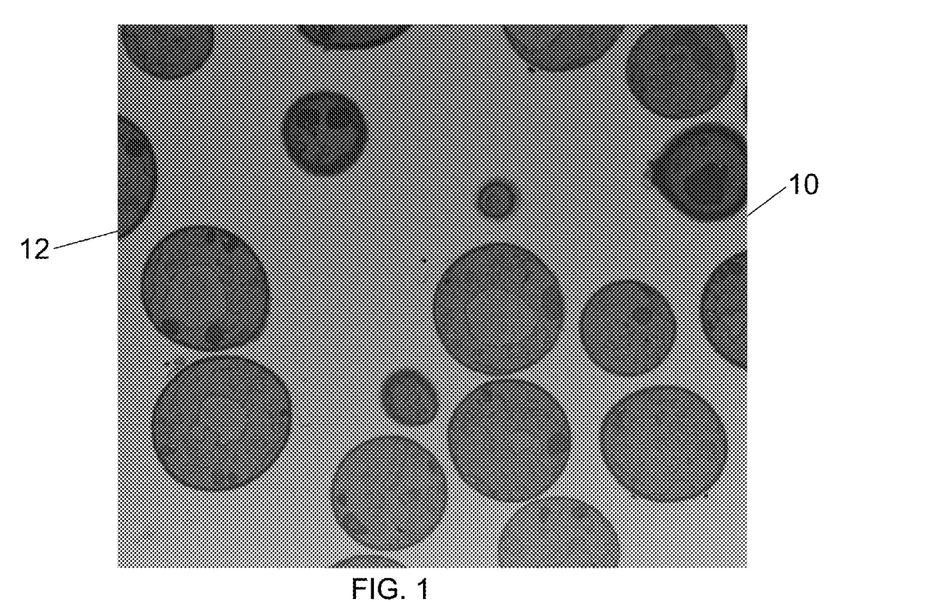
FIG. 1 shows a micrograph of yeast cells set in epoxy.
Figure 2:
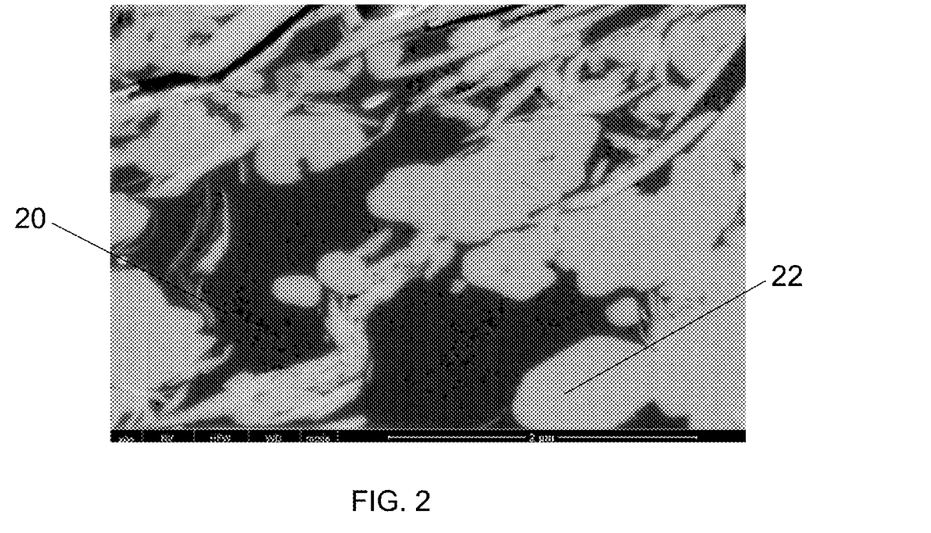
FIG. 2 shows a micrograph of shale interspersed with other mineral substance.

Embodiments of the present invention are directed to methods and apparatuses incorporating methods that reduce the number of data samples that must be acquired in forming an image of a volume. One preferred embodiment relies on the fact that typically in an imaged volume there may be specific portions, representing structures of interest, with the rest of the image data being of little or no value. For example, in FIG. 1, the cells 10 are structures of interest whereas the epoxy mounting medium 12, appearing as a field of light gray in the image is not of interest. In like manner, in FIG. 2 the shale 20 is of interest, whereas the interstitial material 22 which appears as a field of white is not of interest.

In order to avoid scanning, to collect pixel data, in areas that are not of interest a determination must be made, by the data processor that typically forms a part of a scanning image formation device, as to what areas represent structures of interest, and what areas do not, prior to fully scanning an area. In the two examples given by FIGS. 1 and 2, the regions that are not of interest are lighter than the regions of interest. When this is the case, thresholding for darker gray shades and eliminating pixels that are not dark enough (high enough return level) represents one method of discriminating regions of interest from those that are not of interest.

To obtain a preliminary estimate of gray shade value, sufficient to decide whether a pixel is worth further scanning, three techniques may be used, all of which are described in greater detail in the following paragraphs. First, in a system in which a sequence of scans are added together to form an integrated scan, each pixel grayscale in a first scan or a first set of scans can be compared to a threshold to make the determination, which is then applied to subsequent scans of the integrated scan. Second, in the imaging of a volume by an FIB/SEM dual beam system, previously imaged surfaces may have areas that are within the same structure of interest. A biological structure, for example, may extend through many of the progressively revealed surfaces. Accordingly, a determination may be made as to the location of structures of interest in the previous surface, and this information may be used, together with the initial scan data of an integrated scan, to find these structures of interest in surface currently being imaged. Finally, within a single scan, previously scanned pixels may be correlated with prospectively scanned pixels.

Figure 3:
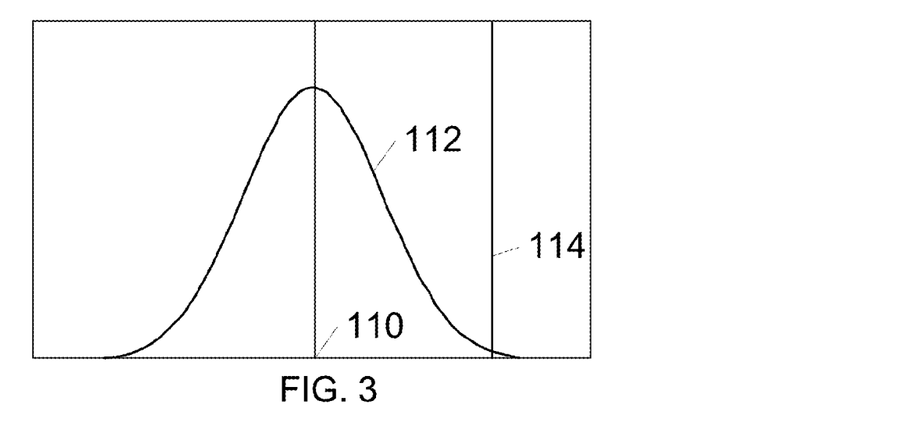
FIG. 3 shows a probability density function of an actual pixel grayscale, given a pixel sample grayscale value, and a threshold set to yield a low probability of falsely finding a low pixel grayscale.
Figure 4:
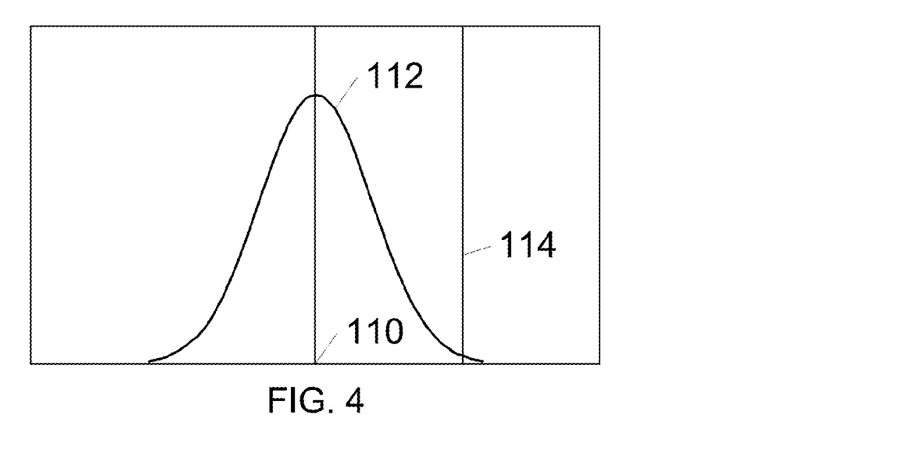
FIG. 4 shows a probability density function of an actual pixel grayscale, given an averaged set of pixel sample grayscale values and a threshold set to yield a low probability of falsely finding a low pixel grayscale.
Figure 5:
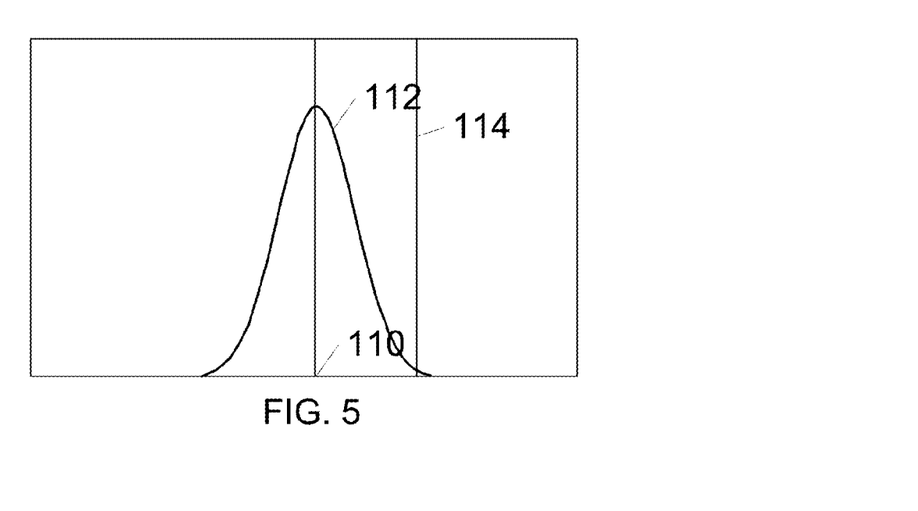
FIG. 5 shows a probability density function of an actual pixel grayscale, given an averaged set of pixel sample grayscale values, wherein the set contains more sample values than the set of FIG. 4, and a threshold set to yield a low probability of falsely finding a low pixel grayscale.

As noted, a scanning electron microscope forms an image by scanning a specimen area multiple (e.g. 20) times with an electron beam while secondary electrons are collected by a secondary electron detector to form an image of the specimen area. This is done to prevent a buildup of charge in any specimen location as the beam dwells at the location. For each scan, there is a measurement of the responsiveness to the beam, that is, the number of secondary electrons collected, for each pixel (that is, a measurement of true pixel grayscale). For the initial scans, these pixel grayscale measurements can be compared to a threshold, to determine if some are of a low enough value that they can be fairly presumed to be from a region that is not of interest. But, referring to FIG. 3, after a single scan (from a series of scans) each such measurement 110 (of a measured value that is exactly at a true pixel grayscale theoretical threshold), has a fairly wide error probability density function (PDF) 112, indicating that it is fairly likely that the actual pixel grayscale is considerably higher than the pixel grayscale measurement. This requires that a conservative threshold 114 be set to avoid falsely deciding to not scan the pixel in the future scans. Referring to FIG. 4, by integrating the scans, for each integrated pixel measurement 110, the error PDF 112 is narrowed and the threshold 114 can be reduced, thereby eliminating more pixels from future scanning. After still more scanning, the PDF is reduced in width still further, as shown in FIG. 5, and a still tighter threshold 114 may be used without too great a chance of excluding a pixel that is actually more intense than indicated by initial scanning.

In a preferred embodiment, this process is continued until either a predetermined number of scans have been performed, or the number of additional pixels excluded by the process falls below a predetermined level. The end of pixel elimination is not necessarily the end of scanning, however, because it may be desirable to continue to collect data to more precisely evaluate pixel grayscales in the regions of interest. In one preferred embodiment, a region having a particularly variegated scan response is scanned an additional number of times, beyond the standard number of scans in an integrated scan, so that even more precise pixel grayscales may be formed in that region. In an alternative preferred embodiment pixels are eliminated from future scanning only after an initial scan, of the integrated scanning process. In an additional alternative preferred embodiment closed forms are detected and included in future scanning, while pixels not inside a closed form are eliminated from future scanning.

In a focused ion beam (FIB)/scanning electron microscope (SEM), the FIB cuts away a partial layer of material and an SEM images the exposed surface. After the initial surface has been imaged, it can be used as a guide, giving a preliminary indication of the location of structures of interest in the immediately subsequent scan. Many specimens include structures of interest that are regularly shaped (for example cells, in a biological specimen) and are larger than the spacing between imaged planes. Accordingly, a pixel occurring outside of a structure of interest in a first imaged plane yields a good indication that the same will be true of a corresponding pixel in a neighboring plane. This information is merged with the information from the first scan or scans from the integrated scanning, to provide an enhanced indicator for whether or not a pixel should be included in a subsequent scan.

Figure 6:
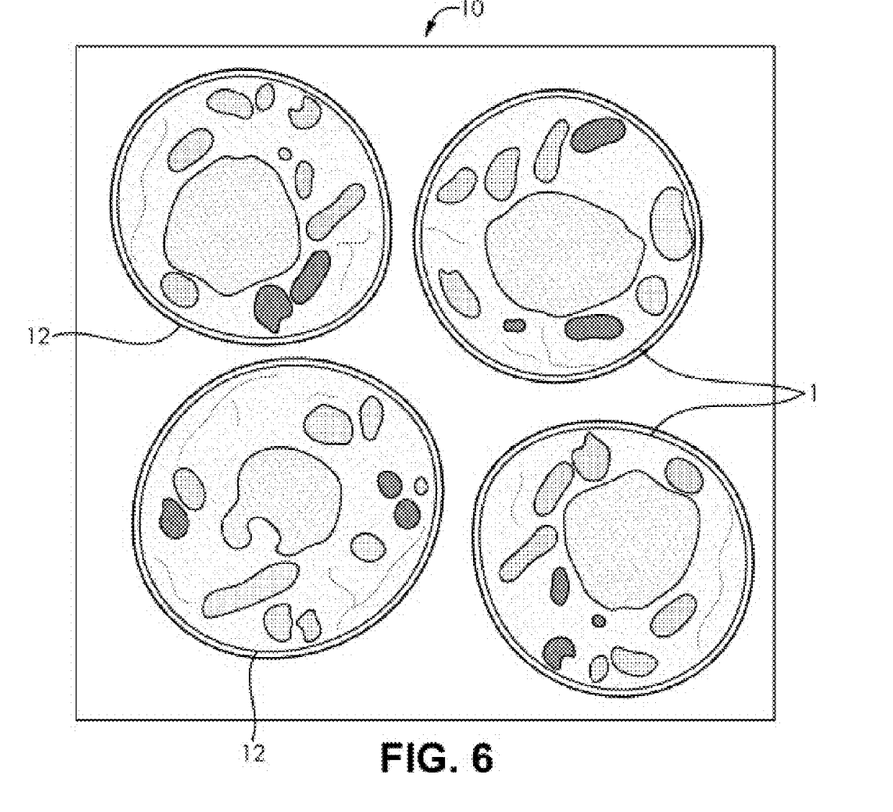
FIG. 6 shows a set of four yeast cells, set in a solid medium and shown in cross-section.
Figure 7:
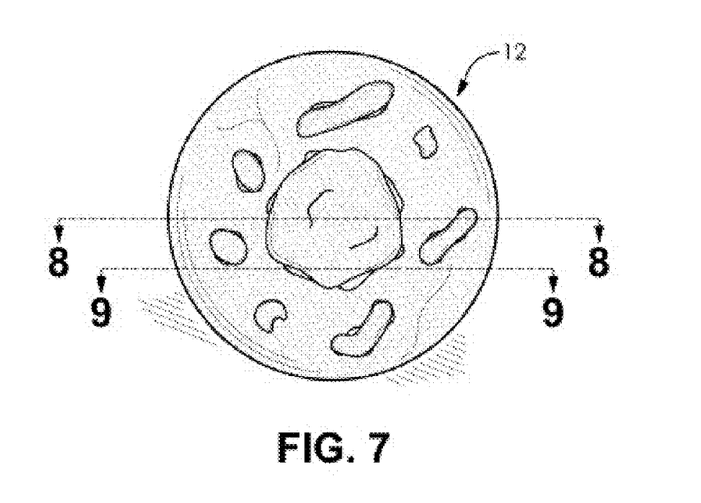
FIG. 7 shows a top view of a yeast cell, having a transparent outer membrane so that the cell organs are visible.
Figure 8:
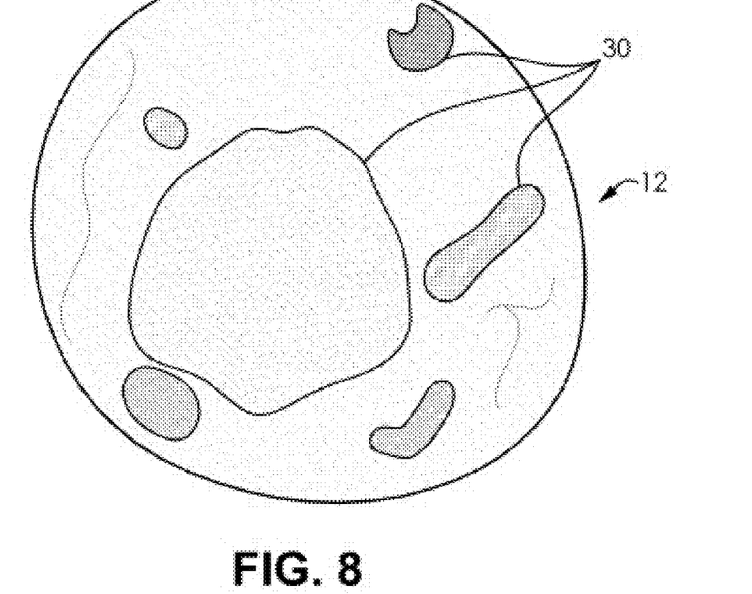
FIG. 8 shows a side-section view of the yeast cell of FIG. 7, taken along line 8-8 of FIG. 7.
Figure 9:
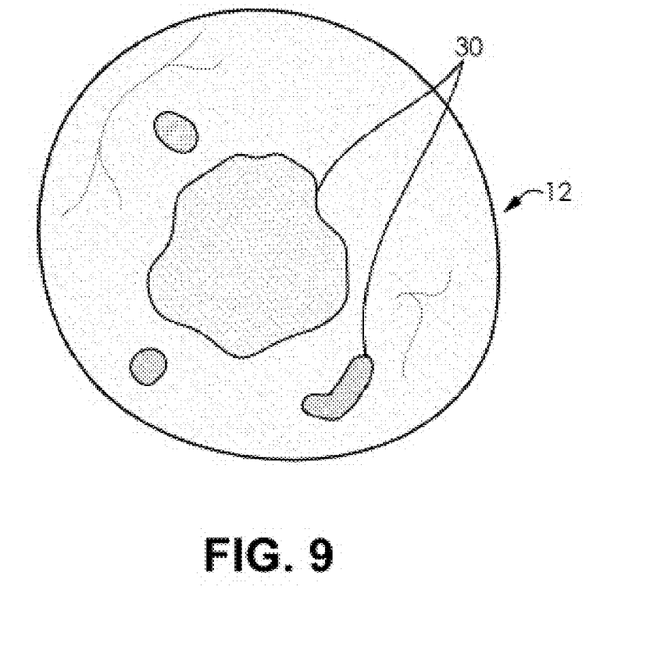
FIG. 9 shows a side-section view of the yeast cell of FIG. 7, taken along line 9-9 of FIG. 7.

FIGS. 6-9 illustrate this point, with FIG. 6 showing a set of four yeast cells set into epoxy, FIG. 7 showing a top view of the upper left one of these cells, and FIGS. 8 and 9 showing closely spaced sections of the cell of FIG. 7, taken along planes 8-8 and 9-9 defined in FIG. 7. A preferred embodiment relies on a correlation between data from a first image plane as illustrated in FIG. 8, and a second image plane as shown in FIG. 9, for the cell 12. As can be seen, there is a general similarity between the two slices, due to their close proximity. This similarity can be harvested by correlating pixels from the cut of FIG. 8, with the prospective evaluation of nearby pixels in the next frame (FIG. 9). The first level effort is to aid in the determination of which pixels represent mere epoxy, as opposed to cell matter 12, and to avoid scanning those areas past the first scan of an integrated scan. In a preferred embodiment, this correlation factor is continued for pixels near the margins of cell 12 as these are the areas have a greater likelihood of not reflecting the region-of-interest value (true or false) of the similarly positioned pixel in the previously scanned plane. In a preferred embodiment pixels that are within the cell boundary are given a very high correlation (0.85) for region-of-interest value in the next plane, and this value declines linearly until a distance of twenty pixels from the cell boundary is reached. In a more advanced embodiment, pixel grayscales may be used to gain a faster evaluation of pixel grayscales in the next scan, for example when a cell organ 30 appears in both scans and is generally the same material.

Additionally, after the beginning of a scan, information from neighboring pixels is correlated with any pixel about-to-be scanned and can be used to increase the certainty of the thresholding to determine if the pixel should be scanned. In a preferred embodiment, to make this decision, a scan other than a straight raster scan is made. For example, a spaced a scan of every tenth row and column of pixels may help determine where the regions of interest are, before performing more detailed scans.

Also, the pixel variance in an area about the pixel of interest, either from an initial scan or set of scans in an integrated scan process, or from previously scanned pixels within the same scan, may be used to determine the presence of a region of interest. This is because a region of interest will tend to have more features than does a background area, such as a volume of undifferentiated epoxy.

Putting together all of the above discussed factors, in a preferred embodiment, used in the scanning of a volume in which regions of interest have higher value pixels than regions that are not of interest and in which areas with higher pixel variance are more likely to represent regions of interest than regions with lower pixel variance, the following thresholding inequality is used to determine which pixels to scan:

$$T < C_R * R + C_{PSF} * (\text{Prev Surface Factor}) + * \Sigma C_{SP}(SP \cdot Px - R) + C_V * (\text{Regional Pixel Variance}) - \epsilon \quad (1)$$

Where:
T=Threshold
$C_R$=Weighting constant for same pixel in previous scans, of an integrated scan
R=Reading of pixel beam responsiveness in previous scans
$C_{PSF}$=Weighting constant for Previous Surface Factor
Prev Surface Factor=1 if pixel is within a region of interest in the neighboring previously scanned surface; =1/#ofpix, where #ofpix=number of pixels separated from a region of interest in the neighboring previously scanned plane, for #ofpix<20; and=0 otherwise.
CSP=Weighting constant for each correlated same scan, same plane, already scanned pixels
SP·Px=correlated, already scanned, same plane pixels
$C_V$=Weighting constant for Regional Pixel Variance
Regional Pixel Variance=Variance of Pixels in a defined area, for example a 100×100 pixel square about the pixel of interest
$\epsilon$=error margin, set to yield a predetermined error rate for falsely categorizing a pixel as not of interest.

Moreover, in a preferred embodiment, even for structures of interest, further scanning for each pixel is stopped when the measurement error for that pixel falls below a threshold. That is, when by taking into account previous surface information, information from previous scans in an integrated scan and previously scanned pixels in the same plane, the system can be certain the pixel's value has been determined to less than a predetermined tolerance, it is not scanned again.

In some situations, it is not possible to use all of the information of Eq. (1). For example, if an integrated scan is not used, the first term "R" will not be available, and any determination to avoid scanning pixels must be made entirely on the basis of correlation to a previously scanned surface or to correlated pixels already scanned in the same plane. Time duration of image formation is not an issue solely in volumetric imaging but is also relevant in mosaic imaging. For example, it may be necessary to collect a gigabyte or more of pixels in the formation of a mosaic image. In this case information from a previous plane is not available, and only the integrated scan and same scan data is available for determining areas to not scan. Finally, even in the same scan, it might not be possible to sufficiently evaluate an immediately scanned pixel, in time to make a decision on whether or not to scan a pixel that is slated to be scanned next. In each of these instances a term is dropped from equation one and $\epsilon$ is increased, to avoid falsely deciding to not scan pixels of interest.

In a preferred embodiment, $C_R$, $C_{PSF}$, $C_{SP}$, $C_V$ and are set according to the type of material to be imaged and the orientation of internal features, which can be entered by a user. For example, if a material having a lot of long features running through the image planes is to be imaged, $C_{PSF}$ is 0 set relatively high, and $\epsilon$ is set relatively low. A user may introduce the material type and orientation of internal features (where appropriate), by a user interface, for example a drop down menu, that would list, for example tissue types, types of core samples. Another drop down menu permits selection of orientation.

As noted previously, in a preferred embodiment, structure of interest (for example, cell) boundaries are detected using either early scans from an integrated scan, previous surface information and/or same scan information. The areas within the boundaries are scanned further, while the areas outside the boundaries are not.

Figure 10:
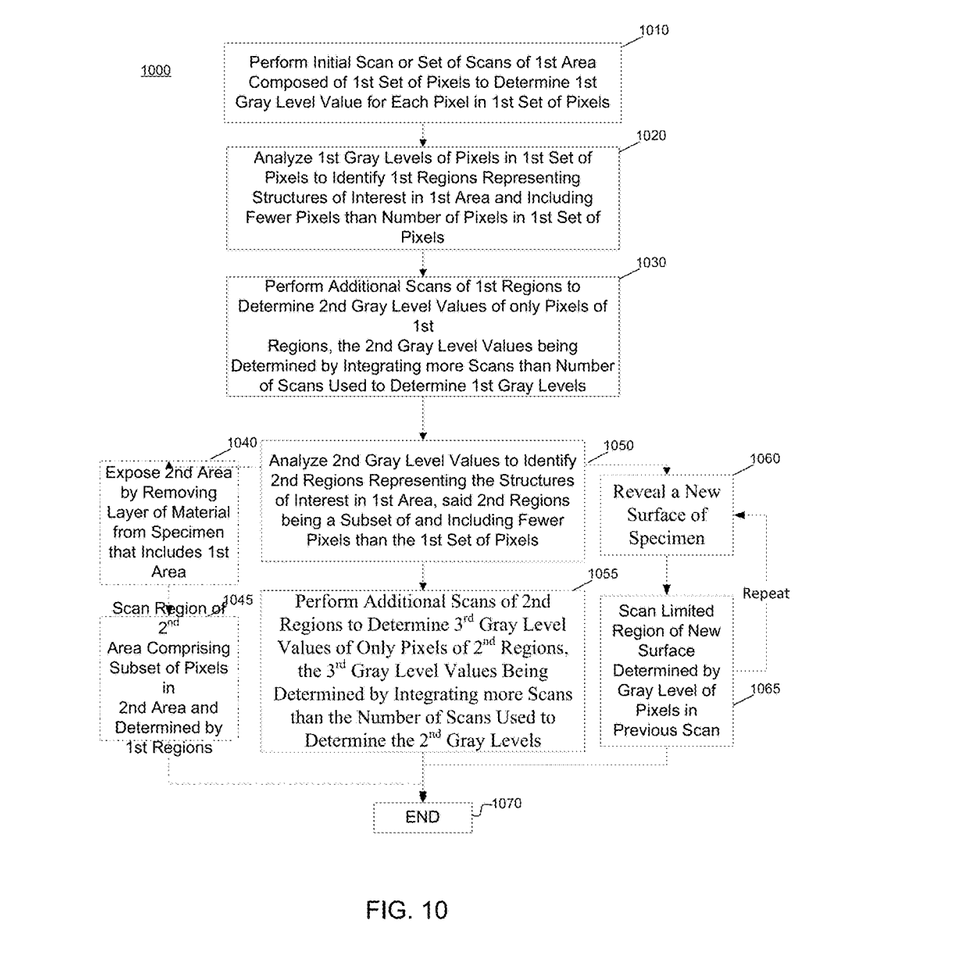
FIG. 10 shows a block diagram of a method of using a scanning microscope to rapidly form an image of a specimen in accordance with an embodiment of the disclosure.

Referring now to FIG. 10, a block diagram of a method 1000 of using a scanning microscope to rapidly form an image of a specimen in accordance with an embodiment of the disclosure is shown. Method 1000 begins at block 1010 by performing an initial scan or set of scans of a first area composed of a first set of pixels to determine a first gray level value for each of the pixels in the first set of pixels.

Method 1000 continues at block 1020 by analyzing the first gray levels of the pixels in the first set of pixels to identify first regions representing structures of interest in said first area, said first regions including fewer pixels than the number of pixels in the first set of pixels. In some embodiments, analyzing the first gray levels of the pixels in the first set to identify first regions includes comparing the first gray level of the pixels to thresholds, the thresholds depending on the number of integrated scans used to determine the first gray levels of the pixels. In some embodiments, analyzing the first gray levels of the pixels in the first set to identify first regions includes comparing the first gray level of the pixels to thresholds, the thresholds depending on the gray level of adjacent levels.

From block 1020, method 1000 continues to block 1030 by performing additional scans using the scanning microscope of said first regions to determine second gray level values of only pixels of said first regions, the second gray level values being determined by integrating more scans than the number of scans used to determine the first gray levels, thereby improving an accuracy of the measured gray level value of pixels in the first regions while including fewer pixels in the additional scans.

In some embodiments, method 1000 continues at block 1040 by exposing a second area by removing from the specimen a layer of material that includes the first area, and then continues at block 1045 by scanning a region of the second area, the region of the second area comprising a subset of pixels in the second area and determined by the first regions. In other embodiments, method 1000 continues at block 1050 by analyzing the second gray level values to identify second regions representing the structures of interest in said first area, said second regions being a subset of and including fewer pixels than the first set of pixels; and then continues at block 1055 by performing additional scans of said second regions using the scanning microscope to determine third gray level values of only pixels of said second regions, the third gray level values being determined by integrating more scans than the number of scans used to determine the second gray levels. In other embodiments, method 1000 continues at blocks 1060 and 1065 by progressively removing material (block 1060) to reveal a new surface and each time a new surface is revealed, scanning (block 1065) a limited region of each new surface, the limited region being determined by the gray level of pixels in a previous scan. In some embodiments, the thresholds are determined by the gray level of neighboring pixels and the gray level of pixels at the same location in a previous surface. Method 1000 ends at block 1070.

Figure 11:
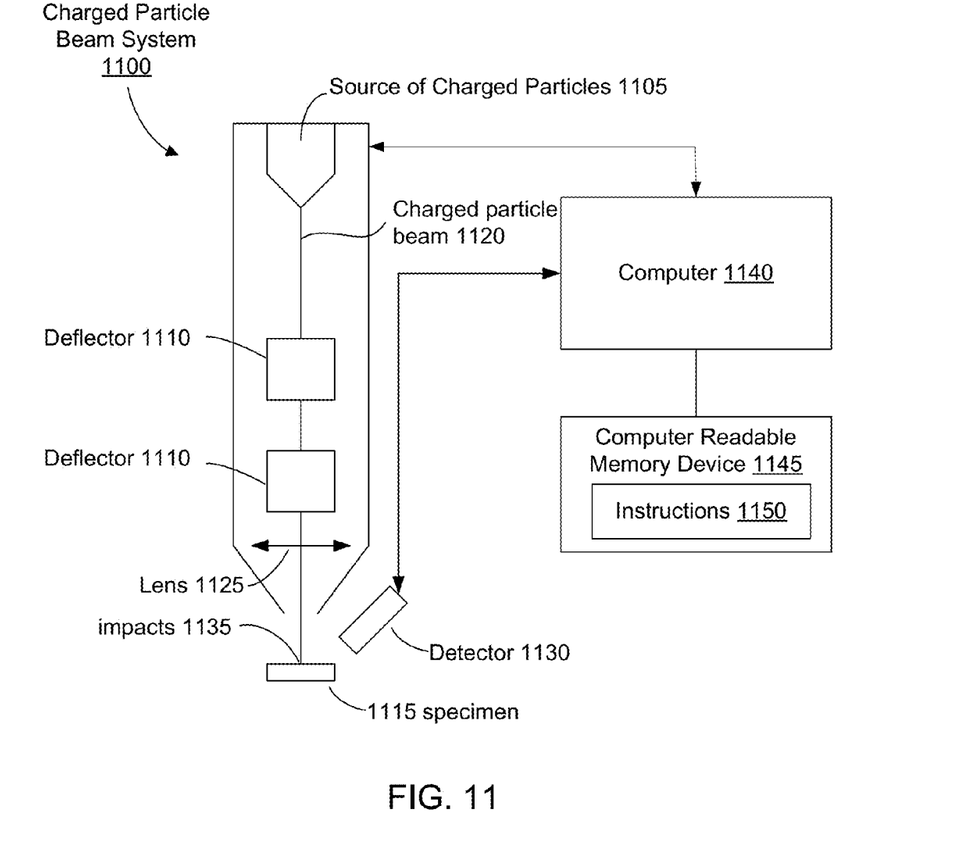
FIG. 11 shows a schematic diagram of a scanning charged particle beam system in accordance with an embodiment of the disclosure.

Referring to FIG. 11, a schematic diagram is shown of an embodiment of a scanning charged particle beam system 1100 configured to carry out method 1000. Scanning charged particle beam system 1100, comprises a source 1105 of charged particles; deflectors 1110 for scanning a specimen 1115 with a charged particle beam 1120; a lens 1125 for focusing the charged particle beam 1120 onto specimen 1115; a detector 1130 for detecting emissions from specimen 1115 in response to impacts 1135 of the charged particles with specimen 1115; a computer 1140 for controlling an operation of scanning charged particle beam system 1100; and a computer readable memory device 1145 that stores instructions 1150 to perform method 1000.

Figure 12:
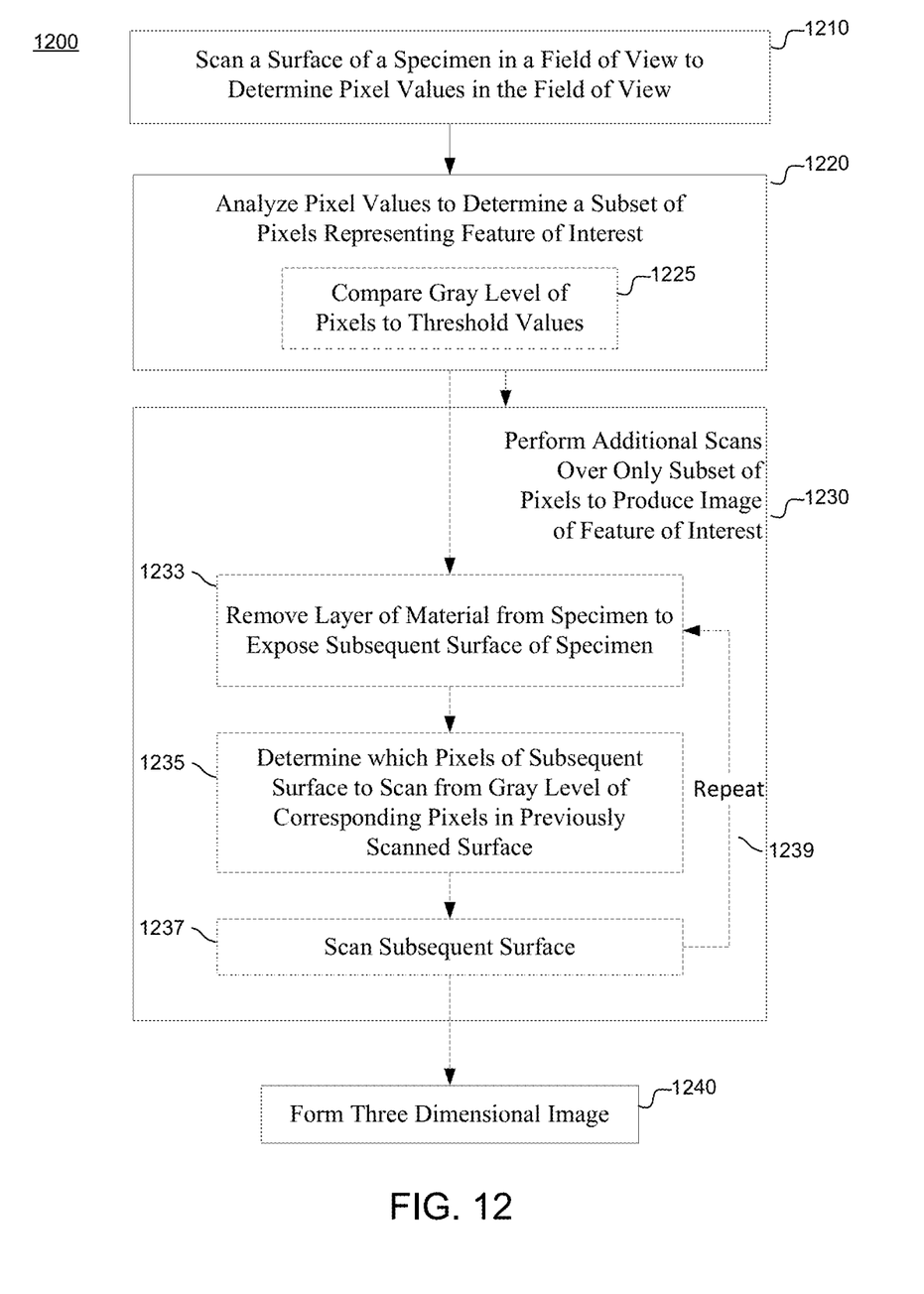
FIG. 12 shows a block diagram of a method of forming an image using a scanning beam in accordance with an embodiment of the disclosure.

Referring now to FIG. 12, a block diagram of a method 1200 of forming an image using a scanning beam in accordance with an embodiment of the disclosure is shown. Method 1200 begins at block 1210 by scanning a surface of a specimen in a field of view to determine pixel values in the field of view.

Method 1200 continues at block 1220 by analyzing the pixels values to determine a subset of pixels that represent a feature of interest. In some embodiments, analyzing the pixels includes comparing the gray level of the pixels to threshold values (block 1225). In some embodiments, the threshold values depend on the number of scans used to determine the pixel values. In some embodiments, the threshold values depend on the gray level of adjacent pixels.

Method 1200 continues at block 1230 by performing additional scans using the scanning beam over only the subset of pixels to produce an image of the feature of interest. In some embodiments, performing additional scans includes removing a layer of material from the specimen to expose a subsequent surface of the specimen (block 1233); and scanning the subsequent surface (block 1237), the pixels of the subsequent surface that are scanned being determined by the gray level of the corresponding pixels in a previously scanned surface (block 1235). In some embodiments of method 1200, removing a layer of material from the specimen to expose a subsequent surface and scanning the subsequent surface using the scanning beam, the pixels of the subsequent surface that are scanned being determined by the gray level of the corresponding pixels in the previously scanned surface is repeated (arrow 1239) to form a three dimensional image (block 1240).

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of using a scanning microscope to rapidly form an image of a specimen, comprising:
    performing an initial scan or set of scans of a first area of the specimen composed of a first set of pixels to determine a first gray level for each of the pixels in the first set of pixels;
    analyzing the first gray levels of the pixels in the first set of pixels to identify first regions representing structures of interest in said first area, said first regions including fewer pixels than the number of pixels in the first set of pixels, wherein analyzing the first gray levels of the pixels includes comparing the first gray level of the pixels to thresholds, the thresholds depending on the gray level of adjacent pixels;
    performing additional scans of said first regions using the scanning microscope to determine second gray level values of only pixels of said first regions, the second gray level values being determined by integrating more scans than the number of scans used to determine the first gray levels, thereby improving an accuracy of the measured gray level value of pixels in the first regions while including fewer pixels in the additional scans; and
    progressively removing material from the specimen to reveal a new surface and each time a new surface is revealed, scanning a limited region of each new surface, the limited region being determined by the gray level of pixels in a previous scan.

2. A scanning charged particle beam system, comprising:
    a source of charged particles;
    deflectors for scanning the specimen with a charged particle beam;
    a lens for focusing the charged particle beam onto the specimen;
    a detector for detecting emissions from the specimen in response to impacts of the charged particles with the specimen;
    a computer for controlling an operation of the scanning charged particle beam system; and
    computer readable memory device that stores instructions to perform the method of claim 1.

3. The method of claim 1 in which the thresholds depend on the gray level of adjacent pixels and on number of integrated scans used to determine the first gray levels of the pixels.

4. The method of claim 1, further comprising:
    exposing a second area by removing from the specimen a layer of material that includes the first area; and
    scanning a second region of the second area, the second region comprising a subset of pixels in the second area and determined by the first regions.

5. The method of claim 1 in which the thresholds are determined by the gray level of neighboring pixels and the gray level of pixels at the same location in a previous surface.

6. A method of forming an image using a scanning beam, comprising:
    scanning a surface of a specimen in a field of view to determine pixel values in the field of view;
    analyzing the pixel values to determine a subset of pixels that represent a feature of interest; and
    performing additional scans using the scanning beam over only the subset of pixels to produce an image of the feature of interest, wherein performing the additional scans includes:

removing a layer of material from the specimen to expose a subsequent surface of the specimen, and scanning the subsequent surface using the scanning beam, the pixels of the subsequent surface that are scanned being determined by the gray level of the corresponding pixels in a previously scanned surf.

7. The method of claim 6 in which analyzing the pixels includes comparing the gray level of the pixels to threshold values.

8. The method of claim 7 in which the threshold values depend on the number of scans used to determine the pixel values.

9. The method of claim 7 in which the threshold values depend on the gray level of adjacent pixels.

10. The method of claim 6 in which removing a layer of material from the specimen to expose a subsequent surface and scanning the subsequent surface using the scanning beam, the pixels of the subsequent surface that are scanned being determined by the gray level of the corresponding pixels in the previously scanned surface, is repeated to form a three dimensional image.

11. A method of using a scanning microscope to rapidly form an image of a specimen, comprising:

performing an initial scan or set of scans of a first area of the specimen composed of a first set of pixels to determine a first gray level for each of the pixels in the first set of pixels;

analyzing the first gray levels of the pixels in the first set of pixels to identify first regions representing structures of interest in said first area, said first regions including fewer pixels than the number of pixels in the first set of pixels;

performing additional scans of said first regions using the scanning microscope to determine second gray level values of only pixels of said first regions, the second gray level values being determined by integrating more scans than the number of scans used to determine the first gray levels, thereby improving an accuracy of the measured gray level value of pixels in the first regions while including fewer pixels in the additional scans;

analyzing the second gray level values to identify second regions representing the structures of interest in said first area, said second regions being a subset of and including fewer pixels than the first set of pixels; and performing additional scans using the scanning microscope of said second regions to determine third gray level values of only pixels of said second regions, the third gray level values being determined by integrating more scans than the number of scans used to determine the second gray levels.

* * * * *

UNITED STATES PATENT AND TRADEMARK OFFICE
CERTIFICATE OF CORRECTION

Page 1 of 1

PATENT NO.        : 9,041,793 B2
APPLICATION NO.   : 13/474176
DATED             : May 26, 2015
INVENTOR(S)       : Cliff Bugge and Brandon van Leer It is certified that error appears in the above-identified patent and that said Letters Patent is hereby corrected as shown below:

In the claims

Claim 6, Column 9, line 6 – Please change "surf" to read --surface--.

Signed and Sealed this
Twenty-seventh Day of October, 2015

Michelle K. Lee
*Director of the United States Patent and Trademark Office*